United States Patent
Dunfield et al.

(10) Patent No.: US 9,687,446 B2
(45) Date of Patent: Jun. 27, 2017

(54) FLUID-JET PENS CONFIGURED FOR MAKING MODULATED RELEASE BIOACTIVE AGENTS

(75) Inventors: John Stephen Dunfield, Corvallis, OR (US); James W. Ayres, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2158 days.

(21) Appl. No.: 12/551,134

(22) Filed: Aug. 31, 2009

(65) Prior Publication Data

US 2009/0317458 A1 Dec. 24, 2009

Related U.S. Application Data

(62) Division of application No. 10/375,399, filed on Feb. 25, 2003, now abandoned.

(51) Int. Cl.
*A61K 9/10* (2006.01)
*A61K 9/127* (2006.01)
*A61K 9/107* (2006.01)
*A61K 9/113* (2006.01)

(52) U.S. Cl.
CPC ............ *A61K 9/10* (2013.01); *A61K 9/1277* (2013.01); *A61K 9/1075* (2013.01); *A61K 9/113* (2013.01)

(58) Field of Classification Search
CPC ............................ A61K 9/107; A61K 9/1075
USPC ........................................ 424/450; 514/937
See application file for complete search history.

(56) References Cited

U.S. PATENT DOCUMENTS

| | | | |
|---|---|---|---|
| 4,268,837 A | 5/1981 | Orzikowski | |
| 5,320,906 A | 6/1994 | Eley et al. | |
| 5,653,996 A | 8/1997 | Hsu | |
| 5,720,551 A | 2/1998 | Shechter | |
| 5,759,566 A | 6/1998 | Poli et al. | |
| 5,786,387 A | 7/1998 | Watanabe et al. | |
| 5,788,972 A | 8/1998 | DeSalvert et al. | |
| 6,102,996 A | 8/2000 | Parazak | |
| 6,261,350 B1 | 7/2001 | Kabalnov | |
| 2002/0064774 A1 | 5/2002 | Schembri et al. | |
| 2003/0044454 A1* | 3/2003 | Fukui et al. ............ | 424/450 |
| 2003/0045467 A1* | 3/2003 | Orban ..................... | 514/12 |

FOREIGN PATENT DOCUMENTS

| | | |
|---|---|---|
| EP | 0260965 | 9/1987 |
| EP | 0916396 | 5/1999 |

OTHER PUBLICATIONS

Donald I. Stimpson et al., "Parallel Production of Oligonucleotide Arrays Using Membranes and Reagent Jet Printing", BioTechniques, v. 25(5), 1998.

* cited by examiner

*Primary Examiner* — Gollamudi Kishore
(74) *Attorney, Agent, or Firm* — Thorpe, North & Western L.L.P.

(57) ABSTRACT

The present invention is drawn to methods of preparing a bioactive agent-containing emulsion for delivery to a biological system. This method can comprise the step of jetting a bioactive agent and a first fluid medium from a fluid-jet pen into a second fluid medium to form a bioactive agent-containing emulsion, wherein the second fluid comprises a continuous phase of the emulsion. Alternatively, a method of preparing a bioactive agent-containing liposome can comprise jetting a lipid-containing composition and a bioactive agent from a fluid-jet pen into a medium to form a bioactive agent-containing liposome carried by the medium. The present invention is also drawn to fluid-jet pens and systems configured for making liposome- and emulsion-containing biological agents.

24 Claims, 2 Drawing Sheets

FLUID-JET PENS CONFIGURED FOR MAKING MODULATED RELEASE BIOACTIVE AGENTS

Figure 1:
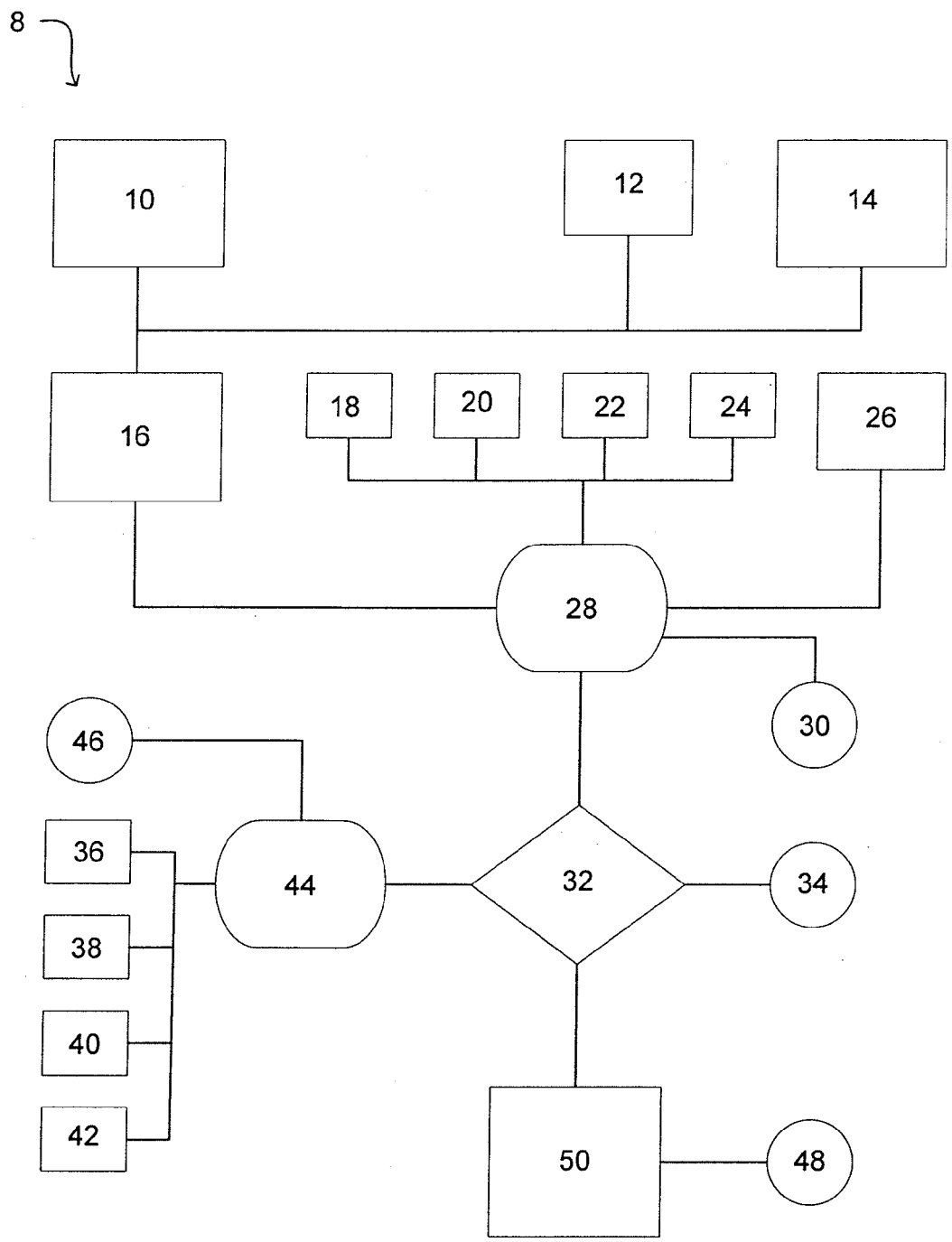

The present application is a divisional of U.S. application Ser. No. 10/375,399, filed Feb. 25, 2003 now abandoned.

FIELD OF THE INVENTION

The present invention is drawn to fluid-jet pens configured for making liposome- and emulsion-containing bioactive agents. The present invention is also drawn to methods for producing bioactive agent-containing emulsions, including microemulsions, as well as bioactive agent-containing liposomes.

BACKGROUND OF THE INVENTION

There have been many approaches to meet the problems of regulating the delivery of bioactive agents, such as drugs, to biological systems including humans, to achieve a proper dose and/or a desired effect. In the prior art, successful bioactive agent delivery vehicles have been designed that are capable of maintaining the bioactive agent in its dissolved state over an extended storage period, and the bioactive agent delivery vehicle itself has been designed to remain stable over a predetermined storage period. Commonly employed delivery vehicles for bioactive agent delivery include lipid emulsions and microemulsions, as well as liposomes and lipospheres compositions.

Emulsion particle or droplet sizes can range from about 200 nm to 1,000 nm. In the prior art, particle size of the lipid emulsions has precluded the use of filters to sterilize such compositions, and thus, heat sterilization has been used. A drawback of the use of heat sterilization is that it can be detrimental to various bioactive agents. Additionally, from a manufacturing standpoint, emulsions have not been preferred for use due to the requirement of the use of the high shear equipment that is presently known, and because emulsions suffer from physical stability problems such as creaming and cracking.

Microemulsions have also been used as bioactive agent delivery compositions. Microemulsions are generally defined as those systems containing a lipophilic and a hydrophilic component wherein the average particle size of the dispersed phase is below about 200 nm. Microemulsions are further characterized as being clear or translucent preparations. The clarity and particle size characteristics distinguish microemulsions from emulsions. The smaller particle size range of microemulsions enables them to be retained in the blood system for a longer period of time than emulsions. Microemulsions are typically more physically stable than emulsions and seldom suffer from creaming or cracking problems, but these phase separation problems may occur during storage under certain conditions.

Liposomes are microscopic vesicles having single or multiple lipid bilayers that can entrap hydrophilic compounds within their aqueous cores. Polar (including hydrophilic) and nonpolar (including hydrophobic) compounds may partition into lipid bilayers. Liposomes have been formed in sizes as small as tens of Angstroms to as large as a few microns, and can be carriers for bioactive agents. Typically, liposomes have been prepared by sonication, detergent dialysis, ethanol injection, French press extrusion, ether infusion, and reverse phase evaporation. These methods often leave residuals such as detergents or organics with the final liposome. Many liposome products are not stable for long periods of time.

Present liposome products can be difficult to sterilize. Sterility is currently accomplished by independently sterilizing component parts (including the lipid, buffer, bioactive agent, and water) such as by the use of an autoclave or by filtration, and then mixing in a sterile environment. This sterilization process can be difficult, time consuming, and expensive since the product must be demonstratively sterile after several processing steps and these methods are not convenient in a retail pharmacy, a doctors office, or in a patients home. Further, sterilizing a formed liposome is usually not feasible as autoclave sterilization can denature the liposome, and filtration can alter the features of multilayered liposomes.

Ink-jet pens have primarily been used in the prior art to form precise patterns of dots in the form of ink-containing images. An ink-jet pen acts by ejecting fluid from a drop-generating device known as a "printhead" onto a printing medium. The typical ink-jet printhead has an array of precisely formed nozzles located on a nozzle plate and attached to an ink-jet printhead substrate. The substrate incorporates an array of firing chambers that receive liquid ink (colorants dissolved or dispersed in a solvent) through fluid communication with one or more ink reservoirs. Each chamber can have a thin-film resistor, known as a "firing resistor," located opposite the nozzle so ink can collect between the firing resistor and the nozzle. The printhead is held and protected by outer packaging referred to as a print cartridge, i.e., ink-jet pen. Upon energizing of a particular resistor element, a droplet of ink is expelled through the nozzle toward the print medium, whether paper, transparent film or the like. The firing of ink droplets is typically under the control of a microprocessor, the signals of which are conveyed by electrical traces to the resistor elements, thereby forming alphanumeric and other characters on the print medium. In the prior art, various emulsion techniques have been implemented in ink-jet ink applications, e.g., both oil-in-water (O/W) and water-in-oil (W/O).

SUMMARY OF THE INVENTION

Because of the nature of emulsions, including microemulsions, and liposomes, there is a need for improvement in the area of making bioactive agent-containing emulsions and liposomes. It has now been recognized that architecture used in the ink-jet arts, i.e., ink-jet pens, can be used to provide mixing, shear, and other forces, and provide additional advantages that are useful in the preparation of bioactive agent-containing liposomes and emulsions.

Specifically, a method of preparing a bioactive agent-containing emulsion for delivery to a biological system can comprise jetting a bioactive agent and a first fluid medium together from a fluid-jet pen into a second fluid medium to form a bioactive agent-containing emulsion. In this embodiment, the first fluid typically becomes part of a discontinuous phase, and the second fluid comprises a continuous phase of the emulsion.

In an alternative embodiment, a method of preparing a bioactive agent-containing liposome can comprise jetting a lipid-containing composition and a bioactive agent, together from a fluid-jet pen into a medium to form a bioactive agent-containing liposome carried by the medium In another embodiment a bioactive material, a surfactant, a nonpolar material, and a polar material are combined and jetted from a fluid-jet pen such that the jetting process either produces an emulsion or reduces the drop size of the internal phase of an existing emulsion.

In a system related to the methods herein, a bioactive agent release system can comprise a fluid-jet pen containing a bioactive agent and a release agent, wherein the fluid-jet pen is configured for jetting the bioactive agent and the release agent, resulting in an association between the bioactive agent and the release agent.

Compositions are also disclosed that are prepared in accordance with each of the methods of the present invention, and include compositions recited both broadly and more narrowly.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

In the accompanying drawings:

FIG. 1 is a block diagram of a method of preparing emulsions in accordance with an embodiment of the present invention; and FIG. 2 is a block diagram of a method of preparing liposomes in accordance with an embodiment of the present invention.

DETAILED DESCRIPTION OF THE PREFERRED EMBODIMENT(S)

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the context clearly dictates otherwise.

Concentrations, amounts, and other numerical data may be expressed or presented herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5% by weight" should be interpreted to include not only the explicitly recited concentration of about 0.1% to about 5% by weight, but also to include individual concentrations and the sub-ranges within the indicated range. Thus, included in this numerical range are individual concentrations such as 2% by weight, 3% by weight, and 4% by weight, and sub-ranges such as from 1% to 3% by weight, from 2% to 4% by weight, from 3% to 5% by weight, etc. This same principle applies to ranges reciting only one numerical value. For example, a range recited as "less than about 5% by weight" should be interpreted to include all values and sub-ranges between 0% and 5% by weight. Furthermore, such an interpretation should apply regardless of the breadth of the range or the characteristics being described.

"Emulsion" generally shall include mixtures of nonpolar materials and polar materials, and can include the presence of an emulsifier and/or a surfactant. Emulsifier and surfactant are terms that may be used interchangeably herein. The term "nonpolar" as applied to materials is well-known in the literature and includes, but is not limited to, materials typically referred to as lipophilic, oils, and materials with a low HLB (hydrophilic-lipophilic balance) value. The term "polar" is also well-known in the literature and includes, but is not limited to, materials typically referred to as hydrophilic, water, and materials with a high HLB (hydrophilic-lipophilic balance) value. Polar and nonpolar includes solids, e.g., drugs with a low water solubility are nonpolar, as well as liquids. Traditionally, emulsions have been defined as compositions that can be subject to separation, creaming, and/or cracking, and define dispersions having particle sizes from about 200 nm to 1000 nm in size. Conversely, microemulsions are compositions that can appear clear, even though they often include similar components as are present in traditionally defined emulsions. However, microemulsions typically include droplets that are smaller in size, i.e., from 5 nm to 200 nm. For purposes of the present invention, when emulsions are referred to, what is meant includes a more general definition including all compositions comprising dispersions of nonpolar-in-polar emulsions, including but not limited to oil-in-water, or polar-in-nonpolar emulsions, including but not limited to water-in-oil. Thus, the term emulsion shall include mixtures of nonpolar materials and polar materials no matter what size of droplets are present, i.e., from the lower end droplet size range of microemulsions to the higher end droplet size range of traditional emulsions. As a result, in accordance with the present invention, the term "microemulsion" defines a range of droplet sizes that is within the lower droplet size range defined by the general term "emulsion." It is also recognized that in some references microemulsions are considered two phase systems with a discontinuous phase and a continuous phase, e.g., polar in nonpolar microdroplets, and other references consider that microemulsions are not true emulsions but are one-phase systems with solubilized nonpolar materials in polar materials, or vice-versa. For purposes of this invention, microemulsions includes both, and both are included when traditional nomenclature such as continuous and discontinuous phases is used herein.

The term "microemulsion" includes nonpolar-in-polar, e.g., oil-in-water (O/W), and polar-in-nonpolar, e.g., water-in-oil (W/O), compositions wherein the dispersion droplet is from >0 nm to 200 nm in size. In one embodiment, an amphiphilic compound, such as a surfactant and/or emulsifier, can be present. In another embodiment, when dealing with emulsions at a microfluidic level, i.e., droplet sizes from 1 to 20 μm in diameter, an amphiphilic compound is not necessarily required, but can optionally be present.

The term "liposome" includes microscopic, and often, spherical vesicles that contain a hydrophilic polar inner core and one or more outer layers comprising lipids, such as phospholipids. The inner core can comprise a bioactive agent, such as a drug. The bioactive agent may alternatively be more closely associated with the lipids than the polar center of the vesicle. A characteristic of liposomes is that they enable water-soluble and water insoluble materials to be used together in a formulation without the requirement of use of surfactants or emulsifiers other than the lipids which form a bilayer, e.g., phospholipids. However, a variety of ingredients can be utilized in production or modification of liposomes as are known in the literature including, but not limited to, neutral or positive charged or negatively charged phospholipids and surfactants. Non-limiting examples of materials used for the preparation of liposomes includes, for example, phosphatidyl choline, phosphatidic acid, phosphatidylglycerol, phosphatidylserine, disteroylphophatidylcholine, dipalmitoylphosphatidylcholine, cholesterol, triolein, stearylamine, 1,2,-bis(hexadecylcycloxy)-3-trimethyaminopropane, N-[1-2,3-dioleyoxy) propyl]-N,N,N-triethyammonium, 1,2-dioleyoxy-3-(trimetylammonium propane), 3-beta-(N,N-dimethylaminoethane)carbamylcholesterol, surfactants, emulsifiers, and polyethylene glycols.

"Fluid-jet pen" includes pen architecture that is substantially similar or the same as that found in the ink-jet arts. Thermal-ink-jet pens or piezo-ink-jet pens provide such examples. The reason the term "fluid-jet pen" is used rather than "ink-jet pen" is because the pens used in accordance with the present invention are optimized for emulsion/microemulsion or liposome jetting and/or production. Modification, if desired, may include design to induce turbulence, multiple fluidic coupling channels which may have mixing chambers, break-up baffles, stirring members, turbulence inducing design, and other mixing structures generally not present in ink-jet pens. No ink per se is typically jetted, though ink may be included as a marker in a formulation along with bioactive material.

"Bioactive agent" includes organic and inorganic drugs, as well as other agents such as proteins and peptides, that are biologically active when introduced to a biological system. Bioactive agent includes at least therapeutics and diagnostics which means any therapeutic or diagnostic agent now known or hereinafter discovered that can be jetted as described herein. Examples of therapeutics, without limitation, are listed in U.S. Pat. No. 4,649,043, which is incorporated herein by reference. Additional examples are listed in the American Druggist, p. 21-24 (February, 1995), which is also incorporated herein by reference. The term "diagnostic" means, without limitation, a material useful for testing for the presence or absence of a material or disease, and/or a material that enhances tissue imaging.

"Biological system" includes a cell, cells, cellular cultures, tissues, organisms, and also includes more advanced systems, such as animals, including humans.

"Lipid-containing composition" or "lipid" can include, but is not limited to, substances known as fats and oils. Fats are triglycerides that are solids at room temperature and oils are all triglycerides that are liquid at room temperature. Lipids are substantially insoluble in water. Examples of lipids that can be used in accordance with the present invention include phospholipids and sterols.

The term "substantially" when used with another term shall include from mostly to completely. Thus, a fluid said to be substantially hydrophobic is hydrophobic to the extent that it generally repels water. However, such a fluid may contain compositional components that are not hydrophobic, though likely such compositions will be present in smaller amounts than the composition providing the hydrophobic characteristic.

The term "association" when referring to a biological agent and a release agent includes physical and chemical attractions or entrapments between the components. This association can be in the context of liposome or an emulsion formation, including microemulsions.

The term "release agent" includes any substance that can be jetted with a bioactive agent that results in an association between the bioactive agent and the release agent. Liposome-forming compositions as well as emulsion-forming compositions are included as release agents.

In accordance with embodiments of the present invention, a method of preparing a bioactive agent-containing emulsion for delivery to a biological system can comprise jetting a bioactive agent and a first fluid medium, together from a fluid-jet pen into a second fluid medium to form a bioactive agent-containing emulsion, wherein the second fluid comprises a continuous phase of the emulsion. In many embodiments, a surfactant can be present in the first fluid medium, or the second fluid medium, or both.

Both polar-in-nonpolar such as water-in-oil (W/O), and nonpolar-in-polar, such as oil-in-water (O/W) emulsions, can be used. In the drug delivery arena, oil-in-water embodiments are more common. However, water-in-oil embodiments can also be used in areas of drug delivery, e.g., oral administration or injections, but are more common in cosmetic applications and the like.

In nonpolar-in-polar embodiments, the first fluid can be substantially hydrophobic, the second fluid can be substantially hydrophilic, and the bioactive agent can comprise a hydrophobic or amphiphilic moiety. In further detail, thermal or piezo fluid-jet architecture can be designed to produce microemulsions underwater, especially in oil-in-water (O/W) embodiments, which are preferred in drug-delivery. In one embodiment, a mixture of drug/surfactant/oil can flow within a reservoir of a fluid-jet pen, and then be ejected from a firing chamber of the pen from the surface or with the orifice immersed in water or another polar environment, in a "drop-on-demand" fashion if desired. Thus, controlled microdroplets can then become surrounded by a continuous external polar, e.g., aqueous phase. Self-alignment of the surfactant can occur at the droplet/continuous interface. In the ink-jet ink arts, a thermal ink-jet pen cannot typically be placed underwater because of pen "drool" or leakage. However, such leakage can be minimized or removed when the pen contains a nonpolar oil material and a drug. Further, for embodiments of this invention, pen architecture and back pressure, if desired, can be modified to minimize drooling of the liquid phase being dispensed by the pen whether the immersion liquid is polar or nonpolar. With this process, very concentrated microemulsions can be produced by continued ejection of a drug and oil, for example, into a fixed volume of an aqueous phase, with rapid stirring and circulation if desired of the continuous phase. This provides an industrial advantage because, in the prior art, production of a concentrated product without (or with minimal) filtration and clean-up has been difficult to obtain.

In polar-in-nonpolar embodiments, the first fluid can be substantially hydrophilic, the second fluid can be substantially hydrophobic, and the bioactive agent can comprise a hydrophilic moiety. Thus, the bioactive agent can be hydrophilic or amphiphilic. This type of emulsion can be used in cosmetic applications, for example, as well as in some drug preparations.

In some embodiments, the bioactive agent can be relatively insoluble in a first phase, and can be prepared as a suspension of microparticulate size, often with a surfactant. This composition can be jetted into the continuous phase to produce an emulsion wherein the discontinuous phase contains microparticulate solids as well as the first liquid phase.

As previously defined, the general term "emulsion" includes both microemulsions and traditionally defined emulsions. However, in one more detailed embodiment, the emulsion can be a microemulsion. One advantage of the present invention is the use of a fluid-jet pen as a homogenizer. Because of the way a fluid-jet pen ejects fluid, microemulsions can be prepared that utilize less surfactant than has been required in the prior art. Many microemulsions utilize about 20% surfactant or more to generate microemulsions. However, by utilizing fluid-jet pen architecture to generate the microemulsions, less surfactant can be required. For example, surfactant can, in general, be present at from 0% to 90% by weight, from 0% to 20% by weight, or even from 0% to 10% by weight, depending on the polarity and characteristics of the liquids/materials and surfactants involved. To obtain microemulsions without the presence of surfactant, i.e., 0% by weight, microemulsions can be generated at a microfluidic level. Further, heat controls within an ink-jet system, especially at the point of drop formation as well as for the entire pen, allows additional control over droplet size and allows introduction of thermal energy. This, in turn, can influence molecular self-alignment and reduce the amount of surfactant needed to produce desired droplet dispersion.

In many applications now available, microemulsions produced are typically designed to be "shelf-stable" for six months or longer. Conversely, with the present invention, a microemulsion can now be produced "on demand" and used within a short time period if desired, thus minimizing the requirement for long shelf life (though microemulsions having a long shelf life can be produced). Thus, microemulsions can be prepared using surfactant amounts that have typically been used to form emulsions having from 200 to 1000 nm droplet size. The use of less surfactant (or even no surfactant on a microfluidic level) can reduce the introduction of side effects associated with surfactant, including diarrhea, reduction of vitamin absorption, localized cell damage such as when applied to nasal tissue, and other known side effects.

The components present in a fluid-jet pen prior to jetting can be stored in a reservoir in many forms. For example, the bioactive agent and first fluid medium can be mixed together, such as in a dispersed state. Alternatively or additionally, further mixing of the bioactive agent and the first fluid medium can occur during jetting. As fluid-jet pen architecture generally includes a firing chamber and very small capillary tubes, the firing chamber can cause turbulence in the capillary tubes, effectuating emulsification. In this embodiment, shear forces provided by the capillary tubes and/or orifice plate can act as a homogenizer, and assist in forming emulsions, or even microemulsions.

In another aspect of the present invention, emulsions can be prepared at a predetermined temperature. In one embodiment, the microemulsion can be prepared at a physiological temperature and immediate delivery to a biological system can be implemented.

The present invention can also be used to generate multiple emulsions. This embodiment can include water-in-oil-in-water emulsions, which are particularly useful with drugs that are difficult to solubilize. For example, an oil can be floated on top of water (layered in the pen), or provided in separate flow channels, and the fluid-jet pen architecture can be configured to feed both of the layers or channels so that when firing occurs, a drop of water inside oil is fired to form a discontinuous phase into a continuous phase of water. In this embodiment, the second fluid medium is the continuous phase of water, and the discontinuous phase is the oil-containing water vesicle formed. The bioactive agent can be associated with the oil-containing water vesicle, and can be in either the oil or the water of the vesicle. A more general embodiment can include the formation of a polar-in-nonpolar-in-polar multiple emulsion. In an alternate embodiment, a similar pen architecture may be used to fire a drop of a first fluid in a layer or channel through a second fluid in a layer or channel such that the product droplets are an emulsion of the first fluid in the second fluid. If the droplets were to be collected and combined, then the first fluid would typically be the discontinuous phase and the second fluid would typically be the continuous phase of the emulsion. But, in this case, the emulsion produced may be delivered directly to a biological system without intermediate collection. This allows formation of the emulsion and delivery of the bioactive agent in the emulsion directly to a patient or tissue at the time of emulsion formation. Typically, a bioactive agent can be included in the discontinuous phase but in some embodiments the bioactive agent can be included in the continuous phase wherein the discontinuous phase contains ingredients that modify or influence the behavior of the bioactive agent. The discontinuous phase may be polar or nonpolar as appropriate, and the continuous phase may be polar or nonpolar as appropriate.

One advantage of the present invention is that bioactive agent-containing emulsions can be prepared on-site for delivery to a biological system. By "on-site," what is meant is that the emulsions can be prepared in a close proximity to a patient or other biological system, just prior to delivery. Examples include: at a doctor's office, at a pharmacy, at a hospital, at a lab where delivery is to occur, e.g., such as to a cellular or tissue culture, etc. Further, several advantages can be realized when delivering the emulsions of the present invention to a biological system, particularly when the biological system is a human patient. For example, droplets of low solubility drugs can be made to be very small, e.g., microemulsions, and therefore, can exhibit increased bioavailability and may demonstrate decreased toxicity. With certain microemulsions, lymphatic absorption can also be effectuated. Further, prolonged emulsion stability is not required since the emulsion can be used soon after preparation or even delivered directly to the patient tissue which, in turn, allows reduction of the amount of surfactant required, if desired, as discussed previously.

In accordance with embodiments of the present invention, the second fluid can also be configured to be within a second fluid-jet pen. Thus, the fluid-jet pen can fire the first fluid into the second fluid, and the resulting emulsion can be fired immediately (or later in time) from the second fluid-jet pen into or onto a carrier medium. The second fluid-jet pen or multiple fluid-jet pens can be combined with the first fluid jet pen within a single structure housing the architecture. The carrier medium can be a liquid substrate, such as oil or water, or can be a substrate, such as a particulate or larger substrate, e.g., an implant. Still further, the carrier medium can be a tissue or cellular site.

Turning to another embodiment of the present invention, a method of preparing a bioactive agent-containing liposome can comprise jetting a liposome forming composition and a bioactive agent, together from a fluid-jet pen into a medium to form a bioactive agent-containing liposome carried by the medium. As is known in the art, liposomes do not form spontaneously, and thus, energy is introduced with a lipid, such as a phospholipid, to effectuate formation. The vesicle developing formulation, e.g., phospholipid, containing a bioactive agent can be fired into an appropriate carrier medium for delivery. By "carrier medium," what is meant is any liquid or solid that acts as a substrate to accept or collect jetted liposomes. One such carrier medium includes an aqueous medium, wherein the drug-containing liposome is jetted into an isotonic solution. If desired, the firing can be directed into a plate or baffles, or sequential firing from one chamber into another and recycling is possible (similar to multiple homogenization passes) prior to final jetting from the pen. Alternatively, the carrier medium can be a solid substrate such as an implant, or can be the ultimate tissue or cellular site that the liposomes are configured to treat or contact. In other words, the medium does not have to be an intermediate application medium, but can be a biological system itself. For example, jetting liposomes containing drugs directly onto/into tissues such as nasal, ophthalmic, or oral mucosal tissues, or other tissues during surgery, can occur. With respect to the bioactive agent, in one embodiment, it can be hydrophilic or amphiphilic. Further, the fluid-jet pen can be a piezo fluid-jet pen or a thermal fluid-jet pen.

Liposomes can be formed for jetting from a fluid-jet pen in a few different ways. For example, a bioactive agent-containing liposome is formed in the fluid-jet pen prior to jetting, such as by treating the fluid-jet pen containing the bioactive agent and the lipid-containing composition with sonication. Thus, after sonication, the fluid-jet pen will contain the bioactive agent-containing liposomes, which can be jetted from the fluid jet pen on demand (similarly, emulsions can be formed in the pen prior to jetting, such as through sonication). Alternatively, a bioactive agent-containing liposome can be formed by the jetting process itself, utilizing forces exerted on compositions during the jetting process. In either embodiment, the step of delivering the bioactive agent-containing liposome to a biological system can be carried out as part of the jetting process, just after jetting, or at a later time, being limited by the length of time such a bioactive agent-containing liposome is considered to be able to provide a therapeutic affect.

In one embodiment, liposomes can be prepared on-site for delivery to a patient or other biological system, minutes or seconds prior to delivery (or as part of the delivery itself). This provides a great advantage in the art of liposome storage and delivery, because storage time can be minimized or eliminated, as liposomes are not typically stable over long periods of time, particularly without the presence of stabilizers, e.g., polyethylene glycol. Liposomes made by sonication agglomerate in just 10 days and even supercritical fluid produced liposomes may agglomerate in 35 days. At least 6 months stability is required by the FDA, usually 2 years is necessary, and 5 years is preferred. "On-site" or "on-demand" formulations that can be provided by the present invention fill a need in the art, particularly since many liposomes are unstable or have a short shelf life. Both single and multiple shell liposomes are known to break down over time, and drug can pass through the shell by diffusion. In fact, it has been difficult to make liposomes that last more than from 24 hours to 6 months, depending on the formulation. In accordance with the present invention, liposomes can be injected into saline, or some other compatible carrier liquid, and delivered without a drying step, or ejected onto a solid support for use, or can be jetted onto mucosal surfaces (mouth, nose, vagina, wounds, veins, etc.), which has not been demonstrated in the prior art. Alternatively, one can jet a liposome onto a patch or onto the skin, and then the liposomes can be covered with a polymer patch, or even overprinted using another fluid-jet pen formulation. Still further, through fluid-jet technology, liposomes can even be driven into the mucosal cells using forces and/or thermal control provided by the fluid-jet pen. It will now readily be recognized that all these applications and more are now available for liposomes, emulsions, and microemulsions.

Turning to another embodiment, a bioactive agent release system can comprise a fluid-jet pen containing a bioactive agent and a release agent, wherein the fluid-jet pen is configured for jetting the bioactive agent and the release agent, resulting in an association between the bioactive agent and the release agent. This system can produce associations in the form of emulsions, including microemulsions, and liposomes. The association can be produced in the fluid-jet pen prior to jetting, such as by sonication or other known processes in the pen or prior to filling the pen such as may be desirable, e.g., for off-axis material feed systems, and the fluid-jet pen is used primarily for delivery purposes. Alternatively, a fluid-jet pen filled with the bioactive agent and the release agent can be sonicated or otherwise mixed or processed prior to firing if desired to pre-form some liposomes or emulsions, depending on the formulation. Alternatively, the association can be produced during jetting itself. Still further, the association can be produced by a combination of premixing or preforming within the fluid-jet pen, and during jetting.

Within the fluid-jet pen, the bioactive agent and the release agent can either be in two separate phases within the fluid-jet pen, such as in layers or such as in a more dispersed mixture or in separate chambers. Under either scenario, the fluid-jet pen containing the bioactive agent and the release agent can be packaged in a sterile or clean environment, thereby providing a sterile association upon jetting from the pen. This is significant in that liposomes and some emulsions cannot be autoclaved for sterilization after production, as such sterilization processes can destroy the bioactive agent, the liposome shell(s), and/or emulsion properties. Thus, fluid-jet pens can be filled with a bioactive agent and releasing agent, i.e., vesicle forming or microemulsion agent and may contain excipients that influence release, and packaged in a sterile manner, thereby removing the need to sterilize upon jetting from the fluid-jet pen at the time of production and delivery to a biological system. Hospitals, pharmacies, or the like, could benefit from such a process. This "point of use" or "on-site" feature of microemulsion and liposome formation using fluid-jet pens also opens applications for "at home" production of compositions for delivery, for example to the nose or mouth, as well as topically. Still further, these formulations can be delivered onto a solid substrate such as inside a capsule or onto a paper or other substrate for ingestion. Other advantages of using a fluid-jet pen as described herein in are on-demand drop delivery at readily controlled frequencies and control of location of drop placement. Production range is from as little as one drop which can be jetted from a single orifice device to large numbers of drops jetted from multiple orifices of ganged-together devices are possible.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Turning now to the Figures, exemplary embodiments that can be used to implement the methods of the present invention are provided.

In FIG. 1, a system 8 of preparing emulsions, including microemulsions, is shown as a flow chart. Flow lines representing movement of ingredients to or from containers or chambers are not numbered but are clearly apparent to one skilled in the art. In this embodiment, a nonpolar formulation 16 can be prepared by combining one or more nonpolar ingredient(s) 10, such as oils, with an optional first excipient 12 and a bioactive material 14. A final nonpolar mixture 28 can then be prepared by combining the nonpolar formulation 16 with one or more other ingredients such as a buffer 18, other excipients 20, surfactants 22, other or additional nonpolar bioactive material 24, and/or solvent 26. Note that the arrangement of the blocks in FIG. 1 represents only one possible sequence of combining materials, and does not require any particular combination or sequence of mixing, but is meant to include many possible combinations and permutations thereof. Further, not all components shown are critical and the number of ingredients is not limited to the number of boxes, as would be known by one skilled in the art after considering the present disclosure.

With the present embodiment, sterilization can occur for the materials before loading into the reservoir chamber or after loading into the reservoir chamber of the pen apparatus. In one embodiment, the final nonpolar mixture 28 can now be contained in the fluid-jet pen reservoir for jetting into a sterile polar mixture 44 to form an emulsion 32 in which the nonpolar mixture is the discontinuous phase and the sterile polar mixture 44 is the continuous phase, as will be described. A variety of materials may be included in forming the polar mixture 44, including polar solvent 36, polar bioactive material 38, buffer 40, and excipient 42. The temperature of polar mixture 44 or the dispensing or jetting of this mixture through an orifice, as is appropriate, can be controlled or regulated by thermal control means 46.

The final nonpolar mixture 28 and the polar mixture 44 can be combined by using thermal control means 34, 46, respectively, as noted above. This can be accomplished by jetting nonpolar mixture 28 under the surface of a rapidly mixing sterile polar mixture 44, thereby forming emulsion 32. The resulting emulsion 32 can be collected or incorporated to form a resulting usable composition 50 which can be in a variety of forms, as desired (via thermal control 34 or some other mechanism). Examples of resulting compositions 50 include fine sprays (nebulize), capsules, surfaces of implantable devices, substrate materials, within a carrier fluid such as part of an IV, or to a tissue cell. Thermal control 48 can also be appropriately placed to enable utilization and/or dispensing of the resulting composition. Thermal control can be carried out in a number of ways, including by using thermal fluid-jetting processes, or by more traditional thermal control methods. As shown, thermal control can optionally be carried at one or more of many steps, such as at steps enumerated at 30, 34, 46, and 48 for example. Other thermal control steps can also be used, as would be know to those skilled in the art.

With respect to one of the embodiments described, a single fluid-jet pen apparatus can be configured such that the final nonpolar mixture 28 can be mixed with the polar mixture 44 within a single fluid-jet pen, and the resulting emulsion 32 produced therein can be dispensed directly, without incorporation into a composition 50, as desired including as an aerosol, as a positive material on the surface of a desired substrate material. In this embodiment (and in others), the dispensing of the final nonpolar mixture to be mixed with a polar mixture may be carried out in such a way that a variety of mixing techniques such as sonication, turbulent flow, and others known in the art, may be employed. Thus, the interior design of a fluid-jet pen may be configured such as to introduce mixing by turbulent flow processes.

In still another embodiment, it is anticipated that the final nonpolar mixture 28 can be delivered into a firing area of a fluid-jet pen, along with the final polar measure in such a way that one mixture "floats" on top of the other mixture. In this embodiment, within the firing chamber, one mixture (28 or 44) can be jetted through the other mixture (44 or 28, respectively), such that an emulsion 32 is produced wherein the first jetted mixture becomes the discontinuous phase and the mixture through which jetting occurs becomes the continuous phase. If jetting an emulsion directly onto a substrate, such as into a fluid substrate or onto a solid substrate, then the emulsion can be prepared prior to jetting. Appropriate architecture for such an embodiment can include a fluid-jet pen that jets a first fluid into the firing chamber of a second fluid-jet pen containing a second fluid. The second fluid-jet pen can be configured to jet the emulsion. Such an embodiment can be characterized by a first fluid-jet pen within a fluid-jet pen, i.e., first pen jets into second pen forming emulsion followed by second pen jetting emulsion. Such an array and utilization can readily be determined by one skilled in the art of fluid-jet pen technology.

Though not shown in FIG. 1, in another embodiment, multiple channels within a fluid-jet pen structure can be designed such that a first liquid is jetted into a second liquid that is jetted through a third liquid using channel and orifice structures appropriate to produce an emulsion of the first liquid in the second liquid in the third liquid. If the first and third liquids are polar (typically aqueous) and the second liquid is nonpolar (typically oil), then a polar-in-nonpolar-in-polar, (typically water-in-oil-in-water) emulsion is produced.

Figure 2:
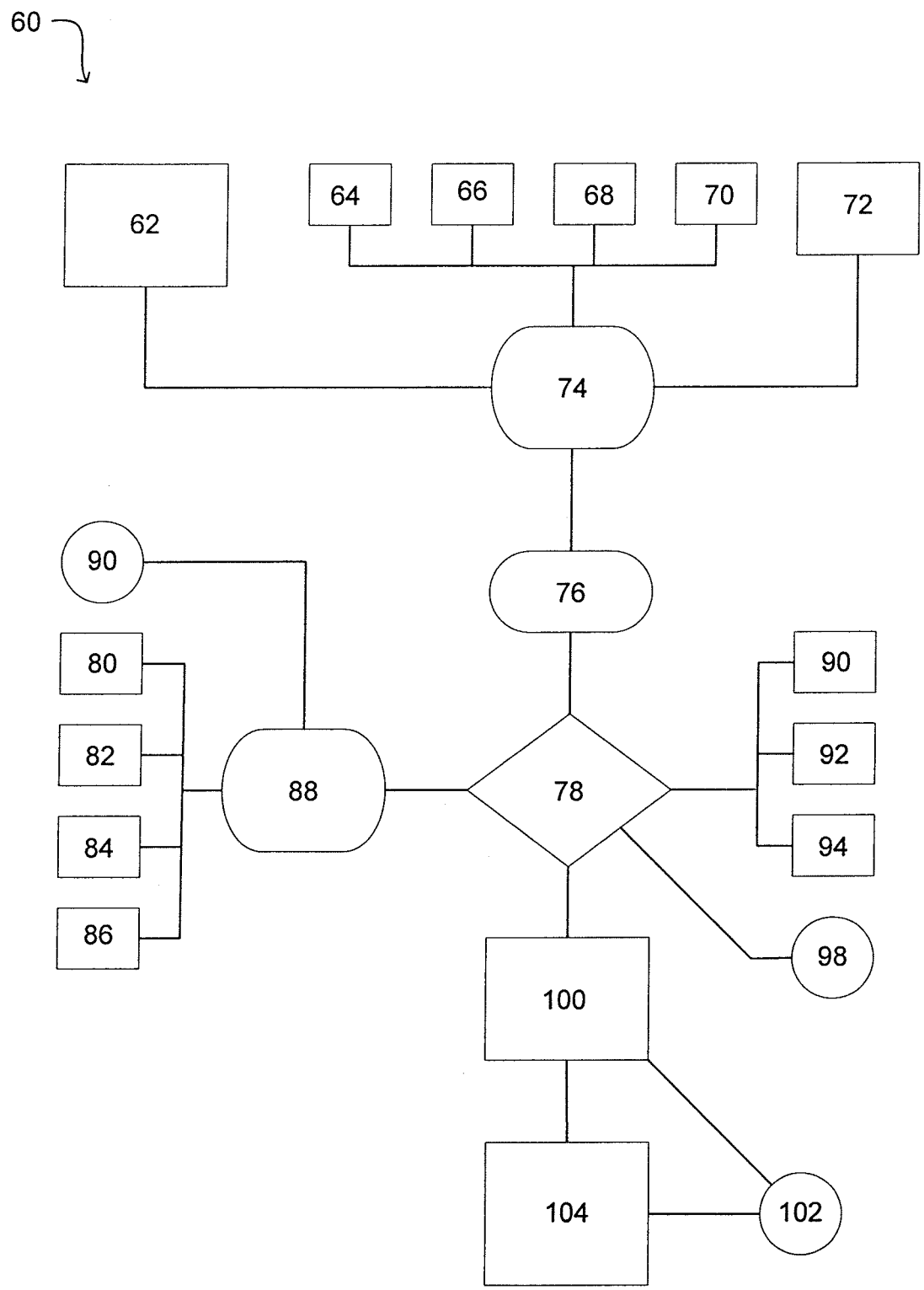

Turning now to FIG. 2, an exemplary embodiment of a system 60 for using a fluid-jet pen to dispense liposomes on site to a target location is provided. Specifically, a lipid formulation 62 can comprise a single lipid or a combination of lipids in a mixture. The lipid(s) of the formulation can be phospholipids involved in formation of any bilayer or multilayer structure of a liposome. The lipid formulation 62 can be combined with other nonpolar materials to form a nonpolar lipid mixture 74. As shown, the other nonpolar materials can include, but are not limited to, buffer 64, excipient 66, surfactant 68, nonpolar bioactive material 70, and typically includes a solvent 72. In one embodiment, the nonpolar lipid mixture 74 can be loaded into an enclosing medium that acts as a reservoir chamber for a fluid-jet pen. The enclosing medium reservoir chamber can be, typically, in an enclosing medium tray or other holding device wherein the tray or other holding device is under the control of a transport mechanism and transport controller. Any conventional technique for aligning parts may be utilized to facilitate loading of the nonpolar lipid mixture 74 into the reservoir chamber. The interior of the reservoir chamber may be a simple walled structure but preferably contains an interior structure that produces a relatively enlarged surface area compared to a simple walled structure. For example, honeycomb structure, separated multi-aligned structure, spiral or circular structure, or another type of structure can be used to increase the amount of contact surface area (sometimes called theoretical plates) within the chamber. A variety of such structures are well-known in the engineering arts.

In the illustrated embodiment, the solvent 72 can be evaporated from the nonpolar lipid mixture 74 to produce a residual film of nonpolar lipid materials 76 on the interior surfaces of a reservoir chamber. Such a chamber can then be flushed with nitrogen if desired and is typically sealed in those cases where a sterile product is desired. All materials can be sterilized prior to filling of the reservoir, either separately or in combination, and the entire process may take place in a sterile environment. Alternatively, the materials may be sterilized after the solvent is evaporated either before or after the pan is sealed. The simplest process that does not result in unacceptable degradation of materials or adverse disruption of the lipid film on the interior surfaces of the reservoir chamber is typically selected. In some cases, the solvent 72 utilized in the process may impart sterility. In any event, a nonpolar lipid material 76 is obtained that can be utilized for further processing I the formation of liposomes.

When production of liposomes is desired, a polar bioactive mixture 88 can be added to a reservoir chamber 78 with the residual film of nonpolar lipid materials 76.

The polar bioactive mixture 88 can be prepared using a polar solvent 80 (typically water), polar bioactive material 82, buffer 84, and excipients 86. Thermal control 90 can also be provided such that the polar solvent comes in contact with the lipid film 76 in the reservoir chamber at a temperature that allows liposome formation, typically within plus or minus 15 degrees centigrade of the glass transition temperature of the liposomal forming lipids, and more typically within 10 degrees of the glass transition temperature of the liposome forming lipids. The polar bioactive mixture 88 can be sterile and can be introduced through a sterilizing filter containing port in the reservoir chamber or elsewhere in the inlet line. Contents of the chamber can be mixed to provide contact between the incoming polar bioactive mixture 88 and the incoming lipid film 76 using one of a variety of mixing methods, as indicated by control boxes, including mixing 90, sonication 92, agitation 94. Also, temperature regulation or thermal jetting or mixing can be enabled by means of thermal control 98. The generated liposomes within the reservoir chamber can be distributed by means of dispenser 100 onto one of many substrates 104 (including fluid and solid substrates), such as to a cellular culture, tissue or a cell, to carrier fluid 104, e.g., IV, for pulmonary delivery, to capsules, to the surface of implantable devices, or to a substrate material, for example. Again, a thermal means 102 can be utilized to regulate dispensing of the liposomes from dispenser 100 or facilitate the delivery of the liposomes to the substrate 104.

In accordance with the present invention, in one embodiment, the liposomes can be dispensed into a carrier fluid that is stored for later use during which storage time does not affect the liposomes in such a way to provide undesirable properties.

In the embodiment described in FIG. 2 above, there are modular components that can be brought together to produce liposomes using, for example, a polar fluid introduced into the pen at a time when liposome production is desired. In another embodiment, a single fluid-jet pen architecture can contain chambers and/or flow channels with jetting and mixing and dispensing controls such that all the liposome formation materials are stored within a single fluid-jet pen albeit in separated chambers such that on activation the polar solvent material stored within the pen is combined with the lipid materials stored within the pen to produce liposomes. The pen architecture can provide jetting of liposomes formed within the pen through one or more orifices into mixing chambers within the pen in a circulating fashion to modify the liposome structure or size prior to movement to another chamber and then jetting liposome formulations out of the fluid-jet pen.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method of preparing a bioactive agent-containing emulsion for delivery to a biological system, comprising jetting:
   (a) a bioactive agent, and
   (b) a first fluid medium,
from a fluid-jet pen into a second fluid medium to form a bioactive agent-containing microemulsion, wherein the second fluid comprises a continuous phase of the microemulsion.

2. A method as in claim 1, wherein the first fluid medium includes a surfactant.

3. A method as in claim 1, wherein the first fluid medium is polar, and the second fluid medium is nonpolar.

4. A method as in claim 1, wherein the first fluid medium is nonpolar, and the second fluid medium is polar.

5. A method as in claim 1, wherein the first fluid is substantially hydrophobic, the second fluid is substantially hydrophilic, and the bioactive agent comprises a hydrophobic moiety.

6. A method as in claim 1, wherein the first fluid is substantially hydrophilic, the second fluid is substantially hydrophobic, and the bioactive agent comprises a hydrophilic moiety.

7. A method as in claim 1, wherein the microemulsion comprises a surfactant present at from 0.1% to 10% by weight.

8. A method as in claim 7, wherein the microemulsion comprises a surfactant present at from 0.1% to 1% by weight.

9. A method as in claim 1, wherein the fluid jet pen is a thermal fluid jet pen.

10. A method as in claim 1, wherein the fluid jet pen is a piezo fluid jet pen.

11. A method as in claim 1, further comprising the step of positioning a jetting orifice of the fluid-jet pen within the second fluid during the jetting step.

12. A method as in claim 1, wherein the bioactive agent and the first fluid medium are in the form of a mixture prior to jetting.

13. A method as in claim 1, wherein the bioactive agent and the first fluid medium are admixed during the jetting step.

14. A method as in claim 1, wherein the fluid-jet pen exerts shear force on the bioactive agent and the first fluid medium during jetting.

15. A method as in claim 1, wherein the bioactive agent-containing microemulsion, and wherein the second fluid has a dropsize from 1 to 20 µm in diameter.

16. A method as in claim 15, wherein the microemulsion is prepared without added surfactant.

17. A method as in claim 1, wherein the microemulsion is prepared at a physiological temperature.

18. A method as in claim 1, wherein the microemulsion formed is a bioactive agent-containing water-in-oil-in-water emulsion.

19. A method as in claim 1, wherein the bioactive agent-containing microemulsion is prepared on-site for delivery to a biological system.

20. A method as in claim 1, further comprising the step of delivering the bioactive agent-containing microemulsion to a biological system.

21. A method as in claim 1, wherein the second fluid is within a second fluid-jet pen, said second fluid-jet pen being configured for firing the microemulsion to a carrier medium.

22. A method as in claim 21, wherein the carrier medium is liquid substrate.

23. A method as in claim 21, wherein the carrier medium is a solid substrate.

24. A method as in claim 21, wherein the carrier medium is a tissue or cellular site.

* * * * *